(12) United States Patent
Van Der Sluis

(10) Patent No.: US 6,504,038 B1
(45) Date of Patent: Jan. 7, 2003

(54) PROCESS FOR THE PREPARATION OF STYRENE AND PROPYLENE OXIDE

(75) Inventor: Jacobus Johannes Van Der Sluis, The Hague (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/743,968

(22) PCT Filed: Jul. 15, 1999

(86) PCT No.: PCT/EP99/05043

§ 371 (c)(1),
(2), (4) Date: Jan. 17, 2001

(87) PCT Pub. No.: WO00/05186

PCT Pub. Date: Feb. 3, 2000

(30) Foreign Application Priority Data

Jul. 20, 1998 (EP) .............................................. 98202428

(51) Int. Cl.⁷ ...................... C07D 301/06; C07D 301/08
(52) U.S. Cl. ......................... 549/518; 585/301; 585/435
(58) Field of Search .......................... 549/518; 585/301, 585/435

(56) References Cited

U.S. PATENT DOCUMENTS

| 5,599,956 A | 2/1997 | Pujado et al. ................ 549/531 |
| 5,756,872 A | 5/1998 | Smith, Jr. et al. ........... 585/449 |

FOREIGN PATENT DOCUMENTS

FR   1460520   2/1967

*Primary Examiner*—T. A. Solola
(74) *Attorney, Agent, or Firm*—Y. Grace Tsang

(57) ABSTRACT

A process for the joint preparation of styrene and propylene oxide comprising the steps of: (a) reacting ethane and benzene to form ethylbenzene; (b) reacting ethylbenzene with oxygen or air to form ethylbenzene hydroperoxide; (c) reacting at least part of the ethylbenzene hydroperoxide obtained with propene in the presence of an epoxidation catalyst to form propylene oxide and 1-phenyl ethanol, and (d) dehydrating at least part of the 1-phenyl ethanol obtained into styrene in the presence of a suitable dehydration catalyst, wherein the ethene used in step (a) and the propene used in step (c) are at least partly provided by a fluid catalytic cracking unit.

9 Claims, 1 Drawing Sheet

PROCESS FOR THE PREPARATION OF STYRENE AND PROPYLENE OXIDE

This application is a 371 of PCT/EP99/05043 filed Jul. 15, 1999.

The present invention relates to a process for the joint preparation of styrene and propylene oxide.

Such process is known in the art and is commonly referred to as styrene monomer/propylene oxide (SM/PO) process. In general, a SM/PO process comprises the steps of:

(a) reacting ethene and benzene to form ethylbenzene, (b) reacting ethylbenzene with oxygen or air to form ethylbenzene hydroperoxide, (c) reacting at least part of the ethylbenzene hydroperoxide obtained with propene in the presence of an epoxidation catalyst to form propylene oxide and 1-phenyl ethanol, and (d) dehydrating at least part of the 1-phenyl ethanol obtained into styrene in the presence of a suitable dehydration catalyst.

The above SM/PO process is well known in the art. In step (a) ethylbenzene is formed by the alkylation of benzene in an ethylbenzene unit. The benzene can, for instance, be derived from a platformer, whilst ethene can be derived from a steam cracking unit. The alkylation reaction may be carried out in various ways known in the art. This reaction can for instance be carried out as a gas phase or liquid phase reaction using an aluminium chloride catalyst-based catalyst. Solid phosphoric acid catalysts or solid acid catalysts based on alumina activated with boron trifluoride are also used in certain benzene alkylation processes for producing ethylbenzene. A further suitable process is the process known as the Mobil/Badger process. In this process a synthetic zeolite catalyst, ZSM-5, is used. In this process the reaction is typically carried out at high temperatures (usually 380–420° C.) and moderate pressure. The preparation of ethylbenzene from ethene and benzene over a zeolitic catalyst is disclosed in U.S. Pat. No. 4,107,224.

Step (a) of the process can be carried out independently from process steps (b) to (d), i.e. at a different location. However, it is preferred that the ethylbenzene production matches the styrene production in step (d), so that the ethylbenzene unit is an integrated part of the SM/PO process or is located in the vicinity of a SM/PO plant. A SM/PO plant with an integrated ethylbenzene unit is generally preferred.

In the oxidation step (b) liquid phase oxidation of ethylbenzene into ethylbenzene hydroperoxide occurs at a temperature of 100–160° C., suitably 130–150° C., and at a pressure of 1–4 bar, suitably 2–3 bar. The oxidation is typically carried out with air as the oxidizing gas, but oxygen may also be applied. The main by-product formed at this stage is acetophenone, which may be hydrogenated in the SM/PO process into 1-phenylethanol, used in step (d) to produce styrene.

In the epoxidation step (c) ethylbenzene hydroperoxide is reacted with propene to yield propylene oxide and 1-phenyl ethanol or substituted 1-phenyl ethanol. In such epoxidation step a homogeneous catalyst or a heterogeneous catalyst can be applied. As homogeneous catalysts molybdenum compounds are frequently applied, while catalysts based on titanium on a silica carrier are often used as heterogeneous catalysts. Conditions under which epoxidation is carried out are known in the art and typically include temperatures of 75 to 150° C. and pressures up to 80 bar with the reaction medium being in the liquid phase. The effluent from the epoxidation step is normally first subjected to a separation treatment to remove the propylene oxide formed, after which the residual stream, containing 1-phenyl ethanol, is suitably subjected to one or more further separation treatments, inter alia to remove ethyl benzene for reuse in an earlier stage of the process. The eventually obtained 1-phenyl ethanol containing stream is then subjected to the dehydration treatment in step (d)

The dehydration of 1-phenyl ethanol into styrene is also well known in the art. It can be carried out both in the gas phase and in the liquid phase. Suitable dehydration catalysts include for instance acidic materials like alumina, alkali alumina, aluminium silicates and H-type synthetic zeolites. Dehydration conditions are also well known and usually include reaction temperatures of 100–210° C. for liquid phase dehydration and 210–320° C., typically 280–310° C., for gas phase dehydration. Pressures usually range from 0.1 to 10 bar. In principle any known dehydration process can be applied in step (d).

In a commercial SM/PO process the propene used in step (c) can be supplied either from an external source or can be made at the SM/PO site itself, normally in a steam cracking unit (also commonly referred to as ethene plant). The latter option is the preferred option and is most frequently applied.

A SM/PO process comprising the steps (a) to (d) as described above requires equal amounts of ethene and propene as feedstock. Because of this, SM/PO plants are typically located in the vicinity of an ethene plant, which produces both the required ethene and propene. Accordingly, if a new SM/PO plant is to be designed and built, this plant is normally either located near an existing ethene plant having an overcapacity of ethene and propene or an ethene plant must be included in the design to ensure the necessary ethene and propene supply. This is not a very advantageous situation from both a logistic and an economic perspective, as it limits the choice of a location for building a SM/PO plant and links the economics to those of an ethene plant. It would, accordingly, be beneficial if ethene and propene could be supplied from an alternative source without having the drawbacks mentioned.

Within the context of the present invention it has been found that integrating a SM/PO process with a fluid catalytic cracking (FCC) unit could overcome the aforesaid economic and logistic constraints.

Accordingly, the present invention relates to a process for the joint preparation of styrene and propylene oxide comprising steps (a), (b), (c) and (d) as described above, wherein the ethene used in step (a) and the propene used in step (c) are at least partly provided by a FCC unit.

A typical FCC unit within the context of the present invention comprises a reactor section and a work-up section. In the reactor section the actual cracking takes place, whereafter in the work-up section the cracked effluent is separated into different products. The reactor section typically comprises a reactor, a catalyst regenerator and a stripper. The temperature in the FCC reactor of the fluid catalytic cracking unit is typically less than about 550° C. and preferably is within the range of from about 500 to about 525° C.

The effluent from the reactor section is then led into the work-up section. Suitably, such work-up section starts with a main fractionator wherein the cracked effluent from the reactor section is introduced. The top fraction of this main fractionator contains the low boiling components, which are mainly C1 to C4 hydrocarbons. Furthermore, gases like hydrogen sulphide, carbonyl sulphide, hydrogen and nitrogen are present in small amounts. This top fraction is typically compressed and routed into an absorption/rectification column. Here the so called off-gas-comprising mainly C1 and C2 components and some hydrogen, nitrogen and sulphur components—is removed and routed, via an unit to remove the sulphur components (typically an amine unit), to the fuel gas system. The C3/C4 material recovered is suitably routed to a debutanizer, a depropanizer and optionally a propane/propene-splitter, where separation into a C4 stream, a propane stream and a propene stream is effected. All treatments starting with the separation in the main fractionator form part of the work-up section.

As indicated above, the off-gas containing the C1 and C2 components from a FCC unit would normally be routed to the fuel gas system. Within the framework of the present invention, however, this off-gas is used as the source of ethene to be used in the ethylbenzene unit. Similarly, the propene used in epoxidation step (c) is derived from the propene/propane-splitter. However, a FCC unit does not produce ethene and propene in the desired ratio of 1:1. It is possible within the framework of the present invention to use the propene and ethene produced in the FCC unit together with ethene and/or propene coming from other sources, preferably located in the vicinity of the SM/PO plant, if the ethene and/or propene production of the FCC unit is not sufficient to meet the ethene and/or propene demand of the SM/PO process.

As stated above, the ethene used in step (a) is suitably derived from the off-gas of the fluid catalytic cracking unit containing the C1 and C2 components. However, it is preferred that the off-gas, after having been passed through an amine unit, is subjected successively to an absorption/desorption treatment for removing hydrogen, nitrogen and methane and to a treatment for removing or hydrogenating acetylene before the resulting stream comprising ethane and ethene is routed to an ethylbenzene producing unit.

It has been found particularly advantageous for the purpose of the present invention that in the ethylbenzene producing unit the stream comprising ethane and ethene is contacted with benzene in the presence of a zeolitic catalyst, suitably a ZSM-5 based catalyst, and that ethylbenzene and remaining ethane are subsequently recovered.

If the ethene produced in the reactor section of the FCC unit is not sufficient to completely fulfil the ethene demand of the SM/PO process, it has been found very useful to produce the remaining part of the ethene needed in one or more cracking furnaces, which are supplied with ethane and optionally propane produced in the reactor section of the fluid catalytic cracking unit. In this way the C2 and C3 products produced in the FCC process are optimally used to create the ethene supply for the ethylbenzene unit. The ethane produced in the FCC unit may be fed directly to the cracking furnace(s). It is, however, preferred to route the ethane as an ethane/ethene stream to the ethylbenzene producing unit, where the ethene is reacted with benzene into ethylbenzene. The remaining ethane is recovered from the ethylbenzene producing unit and is then fed to the cracking furnace(s).

If ethane from the FCC unit alone does not yield sufficient additional ethene from the cracking furnace(s) to supply the necessary ethene, ethane from an external source may be added. If the FCC process yields insufficient propene to fulfil the propene demand of the SM/PO process, the feed to the cracking furnace(s) may also comprise propane recovered from the fluid catalytic cracking unit, optionally supplemented with external propane or even butane. It will be understood that external ethane and/or propane are needed, if so required by the ethene and/or propene demand of the SM/PO process.

In order to make optimal use of the work-up section of the FCC unit and hence to increase the overall process efficiency, it is preferred that the effluent from the cracking furnace(s), which effluent comprises ethene and optionally propene, is worked up in the work-up section of the fluid catalytic cracking unit together with the effluent from the reactor section of the fluid catalytic cracking unit. Said effluent from the cracking furnace(s) normally comprises hydrogen, methane, unconverted ethane and heavier components in addition to a high amount of ethene. If propane is also introduced into the furnace(s), said effluent further comprises propene as well as unconverted propane and heavier components. Thus, the furnace effluent is mixed with the cracked effluent from the reactor section of the FCC unit before entering the main fractionator. In this way, effective separation of propene and ethene is effected and any contaminants and methane formed in the cracking furnaces are removed in the work-up section.

It will be understood that the integration of a FCC unit with a SM/PO process according to the present invention is particularly effective in a situation where a SM/PO plant is to be built simultaneously with a FCC plant at the same location, as this allows an optimally integrated overall design. Alternatively, it can also be effective, although normally less than in the above situation, to build a SM/PO plant at a location where a FCC plant is already present.

BRIEF DESCRIPTION OF THE FIGURES

In FIG. 1 FCC feed (e.g. heavy distillates) enters the FCC reactor section 2. Reactor effluent 3 is subsequently worked up in work-up section 4 resulting in an ethene stream 5 and a propene stream 7. The ethene stream 5 is introduced into ethylbenzene unit 9, optionally with additional ethene 6 from an external source, together with benzene stream 17. The ethylbenzene-containing stream 10 is then led into oxidation unit 11 where the ethylbenzene is oxidized into ethylbenzene hydroperoxide (EBHP) using air or oxygen 18 as the oxidizing gas. The EBHP formed leaves the oxidation unit 11 as stream 12 and is fed into epoxidation unit 13, where it is reacted with propene from propene stream 7 and optionally with propene 8 from an external source to form propylene oxide 19 and 1-phenylethanol 14. The 1-phenylethanol stream 14 is converted in dehydration unit 15 into styrene 16 and water 20.

In FIG. 2 the effluent 2 of the FCC reactor section 1 is passed into main fractionator 3. The top fraction 4 recovered from main fractionator 3 is fed into absorption/rectification column 5, where it is separated into an off-gas stream 7 and a C3/C4 stream 6. The off-gas stream 7 is routed via amine unit 8 (to remove sulphur components), absorption/desorption unit 10 (to remove hydrogen, nitrogen and methane to avoid accumulation of these components in the process), and acetylene removal or hydrogenation unit 13 to ethylbenzene unit 15. The effluent of the amine unit 8 is essentially free of sulphur components, while the stream 12 leaving the absorption/desorption unit 10 is free of nitrogen, NOx, hydrogen and methane, which are all combined into stream 11. The stream 14 leaving the acetylene removal or hydrogenation unit 13 comprises mainly ethane and ethene and is routed to ethylbenzene unit 15, where it is converted into ethylbenzene, leaving as stream 16 to be routed to the oxidation unit of the SM/PO process (not shown). The C3/C4 stream 6 is routed to debutanizer 20, from which a butane/C3 top fraction 21 is recovered. This top fraction 21 is fed into depropanizer 22, where it is separated into butane stream 23 and a C3 stream 24, mainly consisting of propane and propene. Other components present in minor amounts are methylacetylene and propadiene (MA/PD) formed in the cracking furnace(s) 18 and sulphur components. Therefore, the C3 stream 24 is passed through an amine unit 25, whereafter the desulphurized stream 26 is passed through an MA/PD removal or hydrogenating unit 27 yielding a propane/propene stream 28. This propane/propene stream 28 is separated into a propene stream 30 and a propane stream 31 in propane/propene splitter 29. The propene stream 31 can be directly routed to the epoxidation unit of the SM/PO process (not shown). The propane stream 31, optionally supplemented with additional propane 32, is combined with the ethane-containing effluent 17 of the ethylbenzene unit 15. This effluent 17 may be supplemented with external ethane 33. The combined stream is subsequently passed into cracking furnace(s) 18 where cracking into ethene and propene occurs. The ethene/propene containing cracked effluent 19 is then combined with FCC reactor section effluent 2, thus making optimum use of the FCC back-end section already available or to be installed. The ethene from the cracked effluent 19 eventually ends up in ethene/ethane stream 14, while the propene ends up in the propene stream 30.

The invention is further illustrated by the following example without limiting the scope of the invention to this particular embodiment.

EXAMPLE

Figure 1:
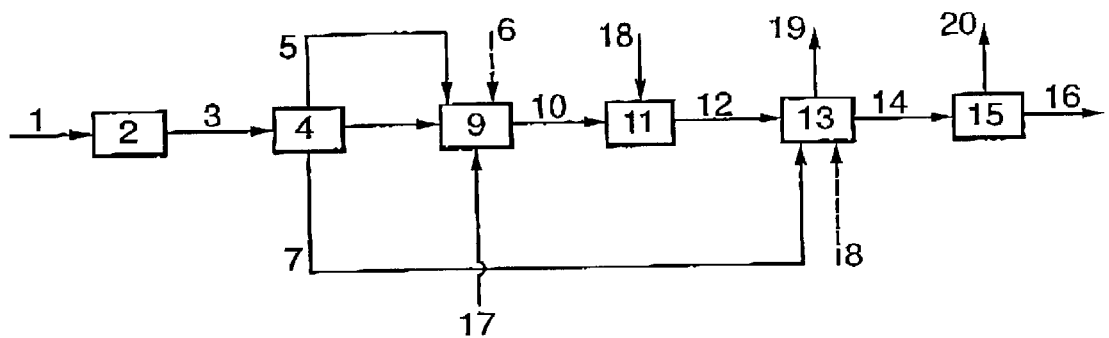
FIG. 1 shows the general concept underlying the present invention.
Figure 2:
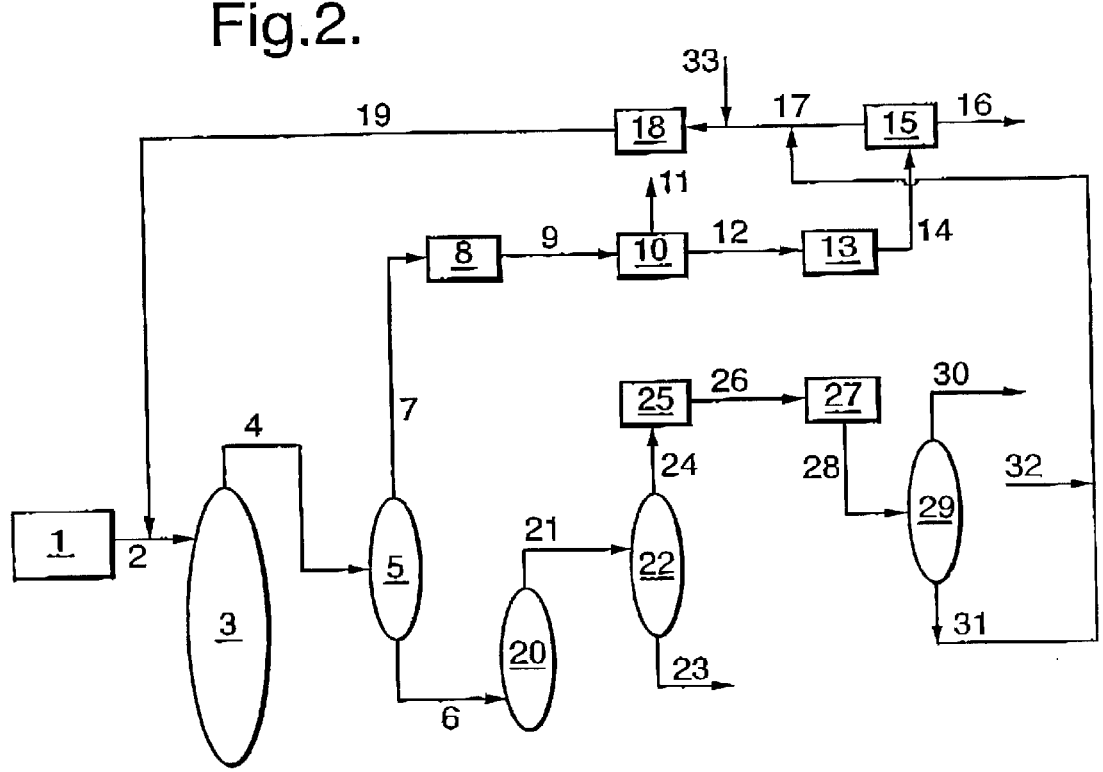
FIG. 2 schematically shows a particularly preferred way of integrating a FCC unit and an ethylbenzene unit for the purpose of the present invention.

The integration between a FCC unit and a SM/PO plant as illustrated by FIG. 2 is carried out using a FCC unit 1 having a feed conversion capacity of 6000 tonnes per day. Three conventional cracking furnaces 18 are used. The integrated process is designed to operate a large scale SM/PO plant requiring an equal amount (12.5 tonnes/hour) of ethene and propene.

In table I the amounts of hydrogen, nitrogen, methane, acetylene, ethane, ethene, propane and propene in the various process streams numbered as indicated in FIG. 2 are given in tonnes/hour (t/h).

As can be seen from table I, the integrated part of the FCC process and the SM/PO process produces the required amount of ethene (12.5 t/h: stream 14), whilst at the same time producing more than enough propene (13.80 t/h: stream 30) to supply the epoxidation section of the SM/PO plant (not shown in FIG. 2) with the required amount of propene.

Thus, it can be seen that the integration between a FCC unit and a SM/PO plant in accordance with the present invention is very well possible without the need for a complete steam cracking unit to supply the required ethene and propene.

TABLE I

Stream compositions

| stream | 2 (t/h) | 19 (t/h) | 2 + 19 (t/h) | 14 (t/h) | 31 (t/h) | 32 (t/h) | 17 + 31 + 32 (t/h) | 30 (t/h) |
|---|---|---|---|---|---|---|---|---|
| hydrogen | 1.80 | 0 | 1.80 | 0 | 0 | 0 | 0 | 0 |
| nitrogen | 0.15 | 0.46 | 0.61 | 0 | 0 | 0 | 0 | 0 |
| methane | 2.85 | 5.02 | 7.87 | 0 | 0 | 0 | 0 | 0 |
| acetylene | 0 | 0.10 | 0.10 | 0 | 0 | 0 | 0 | 0 |
| ethene | 2.20 | 10.22 | 12.42 | 12.50 | 0 | 0 | 0 | 0 |
| ethane | 2.95 | 3.99 | 6.94 | 6.99 | 0 | 0 | 6.99 | 0 |
| propene | 10.78 | 3.03 | 13.80 | 0 | 0 | 0 | 0 | 0 |
| propane | 3.88 | 2.82 | 6.70 | 0 | 6.70 | 13.63 | 20.32 | 13.80 |
| TOTAL | 24.60 | 25.65 | 50.25 | 19.49 | 6.70 | 13.63 | 27.31 | 13.80 |

What is claimed is:

1. A process for the joint preparation of styrene and propylene oxide comprising the steps of:

(a) reacting ethene and benzene to form ethylbenzene, (b) reacting ethylbenzene with oxygen or air to form ethylbenzene hydroperoxide, (c) reacting at least part of the ethylbenzene hydroperoxide obtained from (b) with propene in the presence of an epoxidation catalyst to form propylene oxide and 1-phenyl ethanol, and (d) dehydrating at least a part of the 1-phenyl ethanol obtained from (c) into styrene in the presence of a suitable dehydration catalyst, wherein the ethene used in step (a) and the propene used in step (c) are at least partly provided by a fluid catalytic cracking unit.

2. The process according to claim 1, wherein the ethene used in step (a) is derived from an off-gas of a fluid catalytic cracking unit comprising C1 and C2 components.

3. The process according to claim 2, wherein the off-gas after having been passed through an amine unit, is successively subjected to an absorption/desorption treatment for removing hydrogen, nitrogen and methane and to a treatment for removing acetylene before the resulting stream comprising ethane and ethene is routed to an ethylbenzene producing unit.

4. The process according to claim 3, wherein in the ethylbenzene producing unit the stream comprising ethane and ethene is contacted with benzene in the presence of a zeolitic catalyst, and ethylbenzene and remaining ethane are recovered.

5. The process according to claim 1, wherein one part of the ethene used in step (a) is produced in the reactor section of the fluid catalytic cracking unit and the other part of the ethene needed is produced in one or more cracking furnaces, which are fed with ethane and optionally propane produced in the reactor section of the fluid catalytic cracking unit.

6. The process according to claim 4, wherein the ethane is first routed as an ethane/ethene stream to the ethylbenzene producing unit, after which it is fed to the cracking furnace (s) as the remaining ethane recovered from the ethylbenzene producing unit.

7. The process according to claim 6, wherein the feed to the cracking furnace(s) also comprises propane recovered from the fluid catalytic cracking unit, optionally supplemented with external ethane and/or propane.

8. The process according to claim 5, wherein the effluent from the cracking furnace(s), which effluent comprises ethene and optionally propene, is worked up in the work-up section of the fluid catalytic cracking unit together with the effluent from the reactor section of the fluid catalytic cracking unit.

9. The process according to claim 1, wherein the reactor temperature in reactor section of the fluid catalytic cracking unit is in the range of from 500 to 525° C.

* * * * *